United States Patent [19]

Cracco et al.

[11] 4,125,624
[45] Nov. 14, 1978

[54] ADDUCTS OF BIS(TRI-ALKYLTIN)OXIDE USED AS ACARICIDES

[75] Inventors: Francis J. Cracco, Brussels, Belgium; Wayne I. Fanta, Cincinnati, Ohio

[73] Assignee: The Procter & Gamble Company, Cincinnati, Ohio

[21] Appl. No.: 840,926

[22] Filed: Oct. 11, 1977

Related U.S. Application Data

[63] Continuation of Ser. No. 498,489, Aug. 16, 1974, abandoned, which is a continuation-in-part of Ser. No. 385,129, Aug. 2, 1973, Pat. No. 3,876,795, which is a continuation-in-part of Ser. No. 283,897, Aug. 25, 1972, abandoned.

[51] Int. Cl.$^2$ .............................................. A01N 9/00
[52] U.S. Cl. ..................................................... 424/288
[58] Field of Search ......................................... 424/288

[56] References Cited

U.S. PATENT DOCUMENTS

| 3,264,177 | 8/1966 | Kenaga | 424/288 |
| 3,417,117 | 12/1968 | Davies | 260/429.7 |

Primary Examiner—Leonard Schenkman
Attorney, Agent, or Firm—Ronald L. Hemingway; Richard C. Witte

[57] ABSTRACT

Acaricidal compositions having low toxicity to plants comprising adducts of bis(tri-alkyltin)oxide, wherein the alkyl groups contain from 5–7 carbon atoms, and $CO_2$, CS, or $SO_2$, and an inert carrier. Acaricidal methods comprising contacting plants which are infested by acarids, or which are subject to infestation by acarids, with an acaricidally effective amount of the adducts are also disclosed.

3 Claims, No Drawings

ADDUCTS OF BIS(TRI-ALKYLTIN)OXIDE USED AS ACARICIDES

CROSS-REFERENCE TO RELATED APPLICATION

This application is a continuation of our copending application Ser. No. 498,489, filed Aug. 16, 1974 now abandoned, which was a continuation-in-part of application Ser. No. 385,129, filed Aug. 2, 1973, now U.S. Pat. No. 3,876,795, issued Apr. 8, 1975, which, in turn, was a continuation-in-part of application Ser. No. 283,897, filed Aug. 25, 1972, now abandoned.

BACKGROUND OF THE INVENTION

The present invention relates to the killing of organisms belong to the class acarina, which includes mites and ticks.

Acarids are a serious problem in agriculture and horticulture. These organisms are widely distributed throughout the world and in the United States they are known to attack a wide variety of horticultural and agricultural plants, as well as poultry and livestock.

The bis(trialkyltin)oxides are known to be toxic to insects, acarids, bacteria and other pest organisms. The species of bis(trialkyltin)oxide given widest mention in the literature with respect to pesticidal use is bis(tri-n-butyltin)oxide (TBTO), since this species has apparently been determined to be about optimum with respect to pesticidal activity. TBTO, however, while being an excellent pesticide, has not found wide use in combating pests on agricultural crops, ornamentals or other beneficial plants because it is highly phytotoxic to plants. U.S. Pat. No. 3,264,177 issued to Kenaga on Aug. 2, 1966, discloses that various compounds containing specifically a tricyclohexyltin group, including bis(tricyclohexyltin)oxide, are useful in killing arachnids on plants. Bis(triphenyltin)oxide is described as a fungicide useful on plants in U.S. Pat. No. 3,248,283 issued to Luijten on Apr. 20, 1966.

The adducts of bis(trialkyltin)oxides and compounds such as $CO_2$, $CS_2$, and $SO_2$ are described in the literature as being useful in fungicidal preparations.

SUMMARY OF THE INVENTION

It is an object of this invention to provide novel compositions of matter useful in combating infestations of acarina on plants.

It is an object of this invention to provide a novel method of combating infestations of acarina on plants.

It is a further object of this invention to provide a novel method of preventing the infestation of healthy plants by acarina.

The present invention provides acaricidal compositions comprising one or more compounds (acaricides or toxicants) selected from the group consisting of bis(triacyclicalkyltin)oxides, adducts of bis(tri-alkyltin)oxides with $CO_2$, $CS_2$, and $SO_2$, and mixtures thereof, and an inert carrier. The alkyl groups in the above toxicants contain from five to seven carbon atoms. Acaricidal methods comprising contacting plants infested by acarids, or which are subject to infestation by acarids, with an acaricidally effective amount of the above compositions are also disclosed.

DESCRIPTION OF THE INVENTION

It has now been found according to the present invention that the bis(triacyclicalkyltin)oxides and adducts of bis(trialkyltin)oxides with $CO_2$, $CS_2$, and $SO_2$, wherein the alkyl groups contain from 5 to 7 carbon atoms, have acaricidal activity substantially equivalent to that of TBTO, and at the same time have low phytotoxicity to plants. Accordingly, the present invention provides compositions comprising an organotin compound selected from the group consisting of compounds having the formula $$(R_3Sn)_2O$$

wherein each R is selected from the group consisting of acyclic alkyls containing from 5 to 7 carbon atoms, adducts of one mole of bis(trialkyltin) oxide wherein each alkyl contains from 5 to 7 carbon atoms with one mole of a compound selected from the group consisting of $CO_2$, $CS_2$, and $SO_2$, which adducts may be represented by the formula $$R'_3Sn-O-A(=Z)-Z-SnR'_3$$

wherein R' is alkyl containing from 5 to 7 carbon atoms, Z is selected from the group consisting of oxygen and sulfur, A is selected from the group consisting of carbon and sulfur, and wherein A and Z are different, and mixtures thereof; and an inert carrier. Acaricidal methods comprising contacting plants which are infested by acarina or which are subject to infestation by acarina, with an acaricidally effective amount of the above compositions also comprise part of this invention.

In the conduct of the acaricidal method herein, the acarina are killed by direct contact with the organotin compound when it is applied to the plant, by direct contact with the organotin compound which remains as a residue on the plant, and by ingestion of the tissue of the plant which has been contacted by the organotin compound. The organotin compounds of the invention impart a residual acaricidal effect to the plant so that acarids which infest the plant even days or weeks after application of the compound are killed.

Compositions of matter containing the above described organotin compounds and inert carriers such as powders, granules, and organic solvents, and, optionally, wetting agents and emulsifiers, are suitable for use in the above methods.

Representative bis(tri-acyclicalkyltin)oxides of the invention include bis(tri-n-pentyltin)oxide, bis(tri-n-hexyltin)oxide, bis(tri-n-heptyltin)oxide, bis(tri-2-methylbutyltin)oxide, bis(tri-3-methylpentyltin)oxide, and bis(dihexylpentyltin)oxide. Preferred compounds are bis(tri-n-pentyltin)oxide, bis(tri-n-hexyltin)oxide, bis(tri-n-heptyltin) oxide. The most preferred compound is bis(tri-n-hexyltin) oxide.

Representative adducts of bis(trialkyltin)oxides and $CO_2$, $CS_2$ and $SO_2$ of the invention include the adducts of bis(tri-n-pentyltin)oxide with $CO_2$, bis(tri-n-hexyltin)oxide with $CO_2$, bis(tri-n-heptyltin)oxide with $CO_2$, bis(tri-2-methylbutyltin)oxide with $CO_2$, bis(tricyclohexyltin)oxide with $CO_2$, bis(tri-n-pentyltin)oxide with $CS_2$, bis(tri-n-hexyltin)oxide with $CS_2$, bis(tri-n-heptyltin)oxide with $CS_2$, bis(tri-2-methylbutyltin)oxide with $CS_2$, bis(tri-n-pentyltin)oxide with $SO_2$, bis(tri-n-hexyltin)oxide with $SO_2$, bis(tri-n-heptyltin)oxide with $SO_2$, bis(tri-2-methylbutyltin) oxide with $SO_2$. Preferred compounds are the adducts of bis(tri-n-pentyltin)oxide with $CO_2$, bis(tri-n-hexyltin)oxide with $CO_2$, and bis(tri-n-heptyltin)oxide with $CO_2$. The most preferred compound is the adduct of bis(tri-n-hexyltin)oxide with $CO_2$.

Mixtures of the acaricidal organotin compounds of the invention can be used in place of the single compounds described above. When mixtures are used, the individual toxicants can be present in all relative proportions. Representative mixtures of acaricidal organotin compounds include bis(tri-n-hexyltin)oxide and bis(tri-n-pentyltin) oxide; bis(tri-n-pentyltin)oxide and bis(tri-n-heptyltin) oxide; bis(tri-n-pentyltin)oxide and bis(tri-2-methylbutyltin) oxide; bis(tri-n-heptyltin)oxide and bis(tri-3-methylpentyltin) oxide; bis(tri-n-hexyltin)oxide and bis(dihexylpentyltin)oxide; bis(tri-2-methylbutyltin)oxide and bis(tri-3-methylpentyltin) oxide; bis(tri-n-pentyltin)oxide, bis(tri-n-hexyltin)oxide, and bis(tri-n-heptyltin)oxide; bis(tri-n-pentyltin)oxide, bis(tri-n-heptyltin)oxide, and bis(tri-2-methylbutyltin)oxide; bis(tri-n-pentyltin)oxide, bis(tri-2-methylbutyltin)oxide, and bis(tri-3-methylpentyltin)oxide; the $CO_2$ adduct of bis(tri-n-hexyltin)oxide and the $SO_2$ adduct of bis(tri-n-hexyltin)oxide; the $SO_2$ adduct of bis(tri-n-pentyltin)oxide and the $CO_2$ adduct of bis(tri-n-heptyltin)oxide; the $CO_2$ adduct of bis(tri-n-pentyltin)oxide and the $CO_2$ adduct of bis(tri-n-hexyltin)oxide; the $CO_2$ adduct of bis(tri-n-hexyltin)oxide, the $SO_2$ adduct of bis(tri-n-hexyltin)oxide, and the $CS_2$ adduct of bis(tri-n-hexyltin)oxide; the $CO_2$ adduct of bis(tri-n-hexyltin)oxide, the $SO_2$ adduct of bis(tri-n-pentyltin) oxide, and the $CS_2$ adduct of bis(tri-n-heptyltin)oxide; the $CO_2$ adduct of bis(tri-n-pentyltin)oxide, the $CO_2$ adduct of bis(tri-n-hexyltin)oxide, and the $CO_2$ adduct of bis(tri-n-heptyltin)oxide; bis(tri-n-hexyltin)oxide and the $CO_2$ adduct of bis(tri-n-hexyltin)oxide; bis(tri-n-pentyltin)oxide and the $CO_2$ adduct of bis(tri-n-pentyltin)oxide; and bis(tri-n-hexyltin)oxide, the $CO_2$ adduct of bis(tri-n-hexyltin) oxide, bis(tri-n-pentyltin)oxide, and the $CO_2$ adduct of bis(tri-n-pentyltin)oxide.

A preferred mixture for use in this invention is the mixture of bis(tri-n-pentyltin)oxide and bis(tri-n-hexyltin)oxide. A highly preferred mixture for use in this invention is the mixture of bis(tri-n-hexyltin)oxide and the $CO_2$ adduct of bis(tri-n-hexyltin)oxide. In both of the two immediately preceding mixtures, as is the case in all mixtures of the acaricidal organotin compounds of the invention, the individual components can be present in the mixture in all proportions.

The bis(tri-acyclicalkyltin)oxides of the present invention are known compounds and can be prepared by means well known in the art. For example, one mole of tin tetrachloride can be reacted with 4 moles of the Grignard reagent RMgBr (R being the alkyl desired in the trialkyltin oxide). The resulting tetraalkyltin is then converted to the trialkyltin chloride by reacting it with $SnCl_4$. The trialkyltin chloride is then converted to the bis(tri-acyclicalkyltin) oxide by reacting it with sodium hydroxide. The procedure is more fully described in *J. Appl. Chem.*, Vol. 6, February 1956, pp 49–55.

The adducts of the bis(trialkyltin)oxides of the present invention are known compounds and can be prepared by means well known in the art. A common preparation method is the bubbling of gaseous carbon dioxide through bis(trialkyltin)oxide at 0° to 50° C. at atmospheric pressure. An inert solvent such as n-heptane or xylene can be used to facilitate the reaction. If such an inert solvent is used, it is removed by distillation at the completion of the reaction should its removal be desired. The procedure is more fully described in U.S. Pat. No. 3,417,117 issued to Davies on Dec. 17, 1968, beginning at, for example, Column 2, line 61.

The present invention can be used in combating acarina on all types of useful plants, including field crops such as soybeans, green beans, tomatoes, corn, peppers, strawberries, clover, alfalfa and cotton, orchard crops such as citrus, apples, pears, cherries, grapes and peaches and ornamentals such as evergreens, azaleas, chrysanthemums, roses, carnations and gladiolas. The present invention is particularly advantageous for use on those plants such as soybeans, peaches and certain types of chrysanthemums and roses which are highly prone to give phytotoxic responses when treated with pesticides.

For use as acaricides, the organotin compounds of this invention are preferably incorporated into acaricidal compositions which comprise an inert carrier and one or more of the organotin compounds. (As used herein an inert carrier is defined as a solvent or a dry bulking agent which has substantially no acaricidal effectiveness but which provides a means whereby the organotin compounds can be diluted for convenient application.) Such acaricidal compositions enable the organotin compounds to be applied in a convenient and controlled manner to plants in any desired quantity. These compositions can be solids, such as dusts, or granules or wettable powders, or they can be liquids such as solutions, aerosols, or emulsions. For application to plants, the compositions generally contain from about 50 to 60,000 ppm (parts per million) of the organotin compound depending on the amount of composition applied per acre. When using conventional dilute application techniques, the concentration of organotin compound in the composition will be generally in the range of about 50 to 3000 ppm, preferably about 125 to 1500 ppm. When using the Low Volume (LV) and Ultra Low Volume (ULV) application techniques which have gained wide acceptance in recent years, the concentration of organotin compound in the composition will generally be in the range of 1200 to 36,000 ppm, preferably, from about 2400 to 30,000 ppm. Generally, whatever application technique is used, the amount of organotin compound applied should be of the order of about 0.1 to about 3.0 pounds, preferably about 0.2 to about 2.0 pounds per acre of crop, depending on type of crop, foliage density and the severity of the acarian infestation. For convenience in bulk handling, the compositions are generally formulated as concentrates which can be diluted to the desired usage level with water, solvent or other inert carrier just prior to use.

Dusts can be prepared by blending the organotin compounds with a solid inert carrier such as talcs, clays, silicas, pyrophylite and the like. Granular formulations can be prepared by impregnating the organotin compounds, usually dissolved in a suitable solvent, onto and into granulated carriers such as the attapulgites or the vermiculites, usually of a particle size range of from about 0.3 to 1.5 mm, or by coating a solid inert carrier with a wettable powder formulation of the compounds. Wettable powders, which can be dispersed in water or oil to any desired concentration of the organotin compounds, can be prepared by incorporating wetting agents into concentrated dust compositions.

The organotin compounds of the present invention are sufficiently soluble or dispersible in the common organic solvents such as kerosene, xylene, Stoddard Solvent, acetone, and the like, that they can be used directly as solutions or dispersions in these solvents. Frequently, these solutions or dispersions of acaricide are dispensed under superatmospheric pressure as aerosols. Preferred liquid acaricidal compositions for the practice of the invention herein are emulsifiable concentrates which comprise the organotin compound, an emulsifier, and, as an inert carrier, a solvent. Such concentrates can be extended with water and/or oil to the desired concentration of organotin compound for application as sprays to the plants which are to be treated. The emulsifiers used in these concentrates are surface active agents of the anionic, nonionic, cationic, ampholytic or zwitterionic type and normally comprise from about 0.1% to 30% by weight of the concentrate. The emulsifiers can be used singly or in mixtures. Examples of suitable anionic surface active agents are alkali metal and alkaline earth metal (e.g. sodium and calcium) salts of fatty alcohol sulfates having from 8–18 carbon atoms in the fatty chain and the alkali metal and alkaline earth metal (e.g. sodium and calcium) salts of alkyl benzene sulfonates, having from 9 to 15 carbon atoms in the alkyl chain. Examples of suitable nonionic surface active agents are the polyethylene oxide condensates of fatty alcohols, wherein the fatty chain contains from about 8 to 22 carbon atoms and the amount of ethylene oxide condensed onto each mole of fatty alcohol is from about 5 to 25 moles. Examples of suitable cationic surface active agents are dimethyl dialkyl quaternary ammonium salts wherein the alkyl chains contain from about 8 to 18 carbon atoms and the salt forming anion is a halogen. Examples of suitable ampholytic surface active agents are derivatives of aliphatic secondary or tertiary amines in which one of the aliphatic substituents contains from about 8 to 18 carbon atoms and one contains an anionic water solubilizing group, e.g. sulfate or sulfonate or carboxylate. Specific suitable ampholytic surface active agents are sodium-3-dodecylamino propionate and sodium-3-dodecylamino propanesulfonate. Examples of suitable zwitterionic surface active agents are derivatives of aliphatic quarternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio) propane-1-sulfonate and 3-(N,N-dimethyl-N-hexadecylammonio)-2-hydroxy propane-1-sulfonate. Many other suitable surface active agents are described in McCutcheon's Detergents and Emulsifiers — 1972 Ed., Allured Pub. Co. Ridgewood, N.J., which is incorporated by reference herein. Suitable solvents for these emulsifiable concentrates include hydrocarbons such as benzene, toluene, xylene, kerosene and Stoddard Solvent and halogenated hydrocarbons such as chlorobenzene, chloroform, fluorotrichloromethane and dichlorodifluoromethane. Solvents can be used singly or in mixtures.

The invention will be further illustrated by the following examples. In these examples, acaricidal and plant phytotoxicity test results were obtained according to the following procedures.

Test Procedure I

The plants used for testing were young (approximately 3–4 weeks old) soybean plants, having at least eight fully developed leaves per plant. The acarina organism used was the two-spotted mite, *Tetranychus urticae*.

Initial kill

A mite population of 20–25 mites is allowed to grow for 3 days on a three-leaf cluster on the test plants. At the end of 3 days each plant is sprayed with 15 cc of the acaricidal composition and a count of live adult and immature mites is made at periodic intervals after spraying.

Residual activity — Unwashed

The plants are sprayed with 15 cc per plant of the acaricidal composition. The next day a three leaf cluster on each soybean plant is infested with 10 mites. Counts of live adult and immature mites are made at periodic intervals.

Residual activity — Washed

This test is designed to measure residual activity under circumstances wherein the plant is exposed to water-washing (simulating rain or very high humidity) between the time of spraying and the time of mite infestation. The plants are sprayed with 15 cc per plant of the acaricidal composition. The next day each cluster of leaves which is going to be infested with mites is sprayed with 25 cc of water and allowed to dry. After drying, a three leaf cluster on each soybean plant is infested with 10 mites. Counts of live adult and immature mites are made at periodic intervals.

In each test, untreated control plants are grown adjacent to the test plants and infested with mites in the same manner.

EXAMPLE I

Emulsifiable concentrates were prepared having the following formula:

| Toxicant | 189.25 g. |
| Calcium LAS* | 31.94 |
| TAE$_{11}$** | 31.94 |
| Xylene | 200.48 |

*The calcium salt of linear alkylbenzenesulfonate, the alkyl chain averaging 12 carbon atoms.
**The condensation product of 1 mole of tallow alcohol and 11 moles of ethylene oxide.

In one concentrate, the toxicant was bis(tri-n-butyltin)oxide (TBTO) and in the second, the toxicant was bis(tri-n-hexyltin)oxide (THTO). These concentrates were diluted with water to usage level concentrations and tested for miticidal and phytotoxicity properties on soybean plants in two separate experiments according to the test procedure described above. Results, which are shown in Tables I through IV, indicate that bis(tri-n-hexyltin) oxide has excellent initial and residual acaricidal activity and low plant phytotoxicity, compared to bis(tri-n-butyltin)oxide.

TABLE I

INITIAL KILL
(number of live mites remaining)

| | Toxicant | Toxicant Concentration (ppm) | Days after toxicant application | | | | |
|---|---|---|---|---|---|---|---|
| | | | 0 | 1 | 2 | 11 | 18 |
| Expt. No. 1 | TBTO | 62.5 | 16a | 0 | 31i | 19i | leaves dropped |
| | THTO | 125 | 24a | 1a,1i | 16i | 0 | 0 |
| | Control* | — | 23a | 17a | 19a,30i | TNTC | TNTC |

TABLE I-continued

| | | | INITIAL KILL (number of live mites remaining) | | | | |
|---|---|---|---|---|---|---|---|
| | | Toxicant | Days after toxicant application | | | | |
| | Toxicant | Concentration (ppm) | 0 | 1 | 2 | 11 | 18 |
| Expt. No.2 | TBTO | 125 | 30a | 0 | 0 | 20i | leaves dropped (17 day) |
| | THTO | 250 | 17a | 0 | 0 | 0 | (0) (17 day) |
| | Control* | — | 24a | 23a | 17a | TNTC | (TNTC) (17 day) |

*Plants were infested with 25 mites but no test composition was applied
a = adult mites
i = immature mites
TNTC = too numerous to count

TABLE II

| | | | RESIDUAL ACTIVITY (number of mites remaining) | | | | | |
|---|---|---|---|---|---|---|---|---|
| | | Toxicant | Days after toxicant application | | | | | |
| | Toxicant | Concentration (ppm) | 0 | 1 | 10 | 17 | | |
| Expt. No. 1 | TBTO | 62.5 | 10a | 7a | TNTC | leaves dropped | | |
| | THTO | 125 | 10a | 4a | 16i | 21i | | |
| | Control* | — | 10a | 7a | TNTC | TNTC | | |
| Expt. No. 2 | TBTO | 125 | 10a | 8a | 65i | (leaves dropped) | (16 day) | |
| | THTO | 250 | 10a | 2a | 0 | (0) | (16 day) | |
| | Control* | — | 10a | 9a | 55a&i (combined) | (TNTC) | (16 day) | |

*Plants were infested with 10 mites but no test composition was applied
a = adult mites
i = immature mites
TNTC = too numerous to count

TABLE III

| | | | RESIDUAL ACTIVITY - WASHED (number of mites remaining) | | | | | |
|---|---|---|---|---|---|---|---|---|
| | | Toxicant | Days after toxicant application | | | | | |
| | Toxicant | Concentration (ppm) | 0 | 1 | 10 | 17 | | |
| Expt. No. 1 | TBTO | 62.5 | 10a | 3a | TNTC | leaves dropped | | |
| | THTO | 125 | 10a | 10a | 100i | TNTC | | |
| | Control* | — | 10a | 9a | TNTC | TNTC | | |
| Expt. No. 2 | TBTO | 125 | 10a | 9a | 90i | (leaves dropped) | (16 day) | |
| | THTO | 250 | 10a | 8a | 3i | (3a,4i) | (16 day) | |
| | Control* | — | 10a | 8a | 70a&i (combined) | (TNTC) | (16 day) | |

*Plants were infested with 10 mites but no test composition was applied
a = adult mites
i = immature mites
TNTC = too numerous to count

TABLE IV

| | | | PHYTOTOXICITY GRADE (based on average of 3 plants) | | | | | |
|---|---|---|---|---|---|---|---|---|
| | | Toxicant | Days after toxicant application | | | | | |
| | Toxicant | Concentration (ppm) | 0 | 1 | 2 | 11 | 18 | |
| Expt. No. 1 | TBTO | 62.5 | 0 | 4 | 4.5 | 5 | 5 | |
| | THTO | 125 | 0 | 1 | 0.5 | 0.5 | 1.5 | |
| | Control* | — | 0 | 0 | 0 | 0 | 0 | |
| Expt. No. 2 | TBTO | 125 | 0 | 3 | 4 | 5 | (5) | (17 day) |
| | THTO | 250 | 0 | 0.5 | 0.5 | 1–1.5 | (1.5) | (17 day) |
| | Control | — | 0 | 0 | 0 | 0 | (0) | (17 day) |

*No test composition applied
Phytotoxicity grades  0                5
                No damage →        Heavy damage — plant/leaves essentially destroyed

EXAMPLE II

In another series of experiments, the formula described in Example I was used to prepare emulsifiable concentrates of bis(tri-n-hexyltin)oxide (THTO) and the $CO_2$ adduct of bis(tri-n-hexyltin)oxide (THTCO). These concentrates were diluted with water to usage level concentrations and tested for miticidal and phytotoxicity properties on soybean plants according to Test Procedure I. The results of these tests, as shown in Tables V through VIII, indicate that THTO and THTCO have essentially the same excellent initial and residual acaricidal activity and low phytotoxicity. When the results obtained in this Example II are compared with those obtained in Example I, it is seen that THTCO has excellent initial and residual acaricidal activity and low phytotoxicity as compared to bis(tri-n-butyltin)oxide.

EXAMPLE III

In the second concentrate of Example I, the bis(tri-n-hexyltin)oxide is replaced by an equivalent weight of the following organotin compounds and substantially similar results are obtained in that mite control is substantially equal to or better than that obtained with TBTO, and the phytotoxicity is lower than that observed with TBTO:

bis(tri-n-pentyltin)oxide, bis(tri-n-hepyltin)oxide, bis(tri-2-methylbutyltin)oxide, bis(tri-3-methylpentyltin)oxide, bis(dihexylpentyltin)oxide, and the adducts of bis(tri-n-pentyltin)oxide with $CO_2$, bis(tri-n-hexyltin)oxide with $CO_2$, bis(tri-n-heptyltin)oxide with $CO_2$, bis(tri-2-methylbutyltin) oxide with $CO_2$, bis(tricyclohexyltin)oxide with $CO_2$, bis(tri-n-pentyltin)oxide with $CS_2$, bis(tri-n-hexyltin)oxide with $CS_2$, bis(tri-n-heptyltin)oxide with $CS_2$, bis(tri-2-methylbutyltin)oxide with $CS_2$, bis(tri-n-pentyltin)oxide with $SO_2$, bis(tri-n-hexyltin)oxide with $SO_2$, bis(tri-n-heptyltin) oxide with $SO_2$, bis(tri-2-methylbutyltin)oxide with $SO_2$.

TABLE V

INITIAL KILL
(number of live mites remaining)

| Toxicant | Toxicant Concentration ppm | Days After Toxicant Application | | | | | | |
|---|---|---|---|---|---|---|---|---|
| | | 0 | 1 | 2 | 4 | 7 | 10 | 15 | 18 |
| THTO | 250 | 20 | 0 | 0 | 0 | 2 | 0 | 0 | 0 |
| THTCO | 250 | 20 | 2 | 0 | 2 | 15 | 0 | 0 | 0 |
| THTO | 125 | 21 | 1 | 0 | 11 | 14 | 0 | 0 | 0 |
| THTCO | 125 | 20 | 2 | 0 | 19 | 40 | 10 | 0 | 0 |
| THTO | 62.5 | 19 | 1 | 0 | 17 | 81 | 0 | 0 | 0 |
| THTCO | 62.5 | 20 | 8 | 1 | 25 | 52 | >100 | TNTC | 75 |
| Control | — | 25 | 20 | 18 | >100 | >200 | TNTC | TNTC | TNTC |

TNTC = Too Numerous to Count

TABLE VI

RESIDUAL ACTIVITY - UNWASHED
(number of mites remaining)

| Toxicant | Toxicant Concentration ppm | Days After Toxicant Application | | | | | | |
|---|---|---|---|---|---|---|---|---|
| | | 0 | 1 | 2 | 4 | 7 | 10 | 15 | 18 |
| THTO | 250 | — | 10 | 5 | 4 | 8 | 18 | 3 | 15 |
| THTCO | 250 | — | 10 | 3 | 1 | 0 | 0 | 0 | 0 |
| THTO | 125 | — | 10 | 8 | 5 | 4 | 49 | 84 | >100 |
| THTCO | 125 | — | 10 | 4 | 1 | 1 | 15 | 20 | 75 |
| THTO | 62.5 | — | 10 | 9 | 8 | 8 | >100 | TNTC | TNTC |
| THTCO | 62.5 | — | 10 | 9 | 8 | 7 | 31 | >100 | TNTC |
| Control | — | — | 10 | 10 | 10 | 9 | >100 | TNTC | TNTC |

TNTC = Too Numerous to Count

TABLE VII

RESIDUAL ACTIVITY - WASHED
(number of mites remaining)

| Toxicant | Toxicant Concentration ppm | Days After Toxicant Application | | | | | | |
|---|---|---|---|---|---|---|---|---|
| | | 0 | 1 | 2 | 4 | 7 | 10 | 15 | 18 |
| THTO | 250 | — | 10 | 5 | 0 | 0 | 0 | 0 | 0 |
| THTCO | 250 | — | 10 | 6 | 2 | 1 | 18 | 8 | 15 |
| THTO | 125 | — | 10 | 6 | 2 | 2 | 16 | 25 | 75 |
| THTCO | 125 | — | 10 | 8 | 3 | 1 | 23 | 54 | >100 |
| THTO | 62.5 | — | 10 | 10 | 8 | 6 | 79 | TNTC | TNTC |
| THTCO | 62.5 | — | 10 | 7 | 6 | 5 | 82 | >100 | TNTC |
| Control | — | — | 10 | 8 | 10 | | >100 | TNTC | TNTC |

TNTC = Too Numerous to Count

TABLE VIII

PHYTOTOXICITY GRADES: SOYBEANS
(Based on average of 3 plants)

| Toxicant | Toxicant Concentration ppm | Days After Toxicant Applied | | | | | | |
|---|---|---|---|---|---|---|---|---|
| | | 0 | 1 | 2 | 4 | 7 | 10 | 15 | 18 |
| THTO | 250 | 0 | >0.5 | 0.5 | 1.0 | 2.0 | 2.0 | 2.0 | 2.0 |
| THTCO | 250 | 0 | 0 | >0.5 | >0.5 | 1.0 | 1.5 | 1.5 | 1.5 |
| THTO | 125 | 0 | 0 | >0.5 | 1.0 | 1.5 | 2.0 | 2.0 | 2.0 |
| THTCO | 125 | 0 | 0 | 0 | >0.5 | 0.5 | 1.0 | 1.0 | 1.0 |
| THTO | 62.5 | 0 | 0 | 0 | >0.5 | 0.5 | 0.5 | 0.5 | 0.5 |
| THTCO | 62.5 | 0 | 0 | 0 | 0 | >0.5 | 0.5 | 0.5 | 0.5 |
| Control | — | 0 | 0 | 0 | 0 | 0 | 0 | 0 | 0 |

Phytotoxicity Grades: 0→ No damage
5 Heavy damage (plant, leaves essentially

TABLE VIII-continued

PHYTOTOXICITY GRADES: SOYBEANS
(Based on average of 3 plants)

| Toxicant | Toxicant Concentration ppm | Days After Toxicant Applied | | | | | | |
|---|---|---|---|---|---|---|---|---|
| | | 0 | 1 | 2 | 4 | 7 | 10 | 15 | 18 | destroyed)

EXAMPLE IV

In the second concentrate of Example I, the bis(tri-n-hexyltin)oxide is replaced with an equivalent weight of the following mixtures of compounds and substantially similar results are obtained in that the mite control is substantially equal to or better than that obtained with TBTO and the phytotoxicity is lower than that observed with TBTO: bis(tri-n-hexyltin)oxide and the $CO_2$ adduct of bis(tri-n-hexyltin)oxide wherein the weight ratio of the two materials is 1:1; bis(tri-n-hexyltin)oxide and the $CO_2$ adduct of bis(tri-n-hexyltin)oxide wherein the weight ratio of the two materials is 10:1; bis(tri-n-hexyltin)oxide and bis(tri-n-pentyltin)oxide wherein the weight ratio of the two materials is 2:1; the $CO_2$ adduct of bis(tri-n-hexyltin)oxide and the $CO_2$ adduct of bis(tri-n-pentyltin)oxide wherein the weight ratio of the two materials is 2:1; and bis(tri-n-hexyltin)oxide, the $CO_2$ adduct of bis(tri-n-hexyltin)oxide, bis(- tri-n-pentyltin)oxide, and the $CO_2$ adduct of bis(tri-n-pentyltin)oxide wherein the weight ratio of the four materials is 10:1:5:0.5.

A second series of tests was conducted to further illustrate this invention.

Test Procedure II

Lima bean plants are infested with 50 to 100 adults of the strawberry spider mite (*Tetranychus atlanticus*). Infested plants are dipped into solutions of the test material. Adult mortality is noted.

EXAMPLE V

Emulsifiable concentrates were prepared as in Example I. In three separate concentrates, the toxicants were bis(tri-n-hexyltin)oxide (THTO), bis(tri-n-pentyltin) oxide (TPTO), and bis(tri-n-heptyltin)oxide (THpTO). The results of the tests with strawberry spider mites at the concentration noted are shown in Table IX. These results show these materials to be effective acaricides. No substantial phytotoxicity was observed.

EXAMPLE VI

The concentrate formula of Example I was used with the Test Procedure II to further show the efficacy of bis(tri-n-hexyltin)oxide and its $CO_2$ adduct. The results shown in Table X indicate THTCO is an excellent acaricide. No substantial phytotoxicity was reported for either material.

TABLE IX

ADULT MORTALITY AFTER 5 DAYS
(based on average of 3 replications)

| Toxicant | % Mortality |
|---|---|
| 0.05% W/V* | |
| TPTO | 100 |
| THTO | 100 |
| THpTO | 92 |
| 0.025% W/V | |
| TPTO | 100 |
| THTO | 100 |
| THpTO | 11 |
| 0.0025% W/V | |
| TPTO | 100 |
| THTO | 97 |
| THpTO | 0 |
| 0.001% W/V | |
| TPTO | 81 |
| THTO | 85 |
| THpTO | 0 |

*weight/volume

TABLE X

| | ADULT MORTALITY | |
|---|---|---|
| Toxicant | | % Mortality |
| 0.005% W/V | | |
| THTO | | 100 |
| THTCO | | 100 |
| 0.0005% W/V | | |
| THTO | | 62 |
| THTCO | | 100 |
| 0.00005% W/V | | |
| THTO | | <13 |

TABLE X-continued

| ADULT MORTALITY | |
|---|---|
| THTCO | 32 |

EXAMPLE VII

Wettable powders are prepared having the following formula:

| Toxicant | 100 g. |
|---|---|
| *Powdered Active Clay | 240 |
| **Anionic Wetting Agent | 60 |

*Such as Clarolite T-60, sold by the Georgia Kaolin Company.
**Sodium alkylaryl sulfonate wherein the alkyl chain averages 12 carbon atoms.

In a series of wettable powders, the toxicant is respectively bis(tri-n-hexyltin)oxide, the $CO_2$ adduct of bis(tri-n-hexyltin)oxide, bis(tri-n-pentyltin) oxide, the $CO_2$ adduct of bis(tri-n-pentyltin)oxide; a mixture of bis(tri-n-hexyltin)oxide and the $CO_2$ adduct of bis(tri-n-hexyltin)oxide wherein the two components are present in a weight ratio of 1:1, a mixture of bis(tri-n-pentyltin)oxide and the $CO_2$ adduct of bis(tri-n-pentyltin) oxide wherein the two components are present in a weight ratio of 1:1. These wettable powders are dispersed in water to usage level concentrations and tested for miticidal and phytotoxicity properties on soybean plants according to Test Procedure I. The results of these experiments show that all of the wettable powders demonstrate mite control substantially equal to that obtained using the second emulsifiable concentrate of Example I and that the phytotoxicity observed is substantially equivalent to that of the second emulsifiable concentrate of Example I.

What is claimed is:

1. A method of killing acarids comprising the contacting of said acarids or their plant habitats with an acaricidally effective non-phytotoxic amount of an acaricide represented by the formula

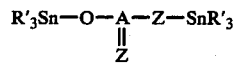

wherein R' is alkyl containing from 5 to 7 carbon atoms, Z is selected from the group consisting of oxygen and sulfur, A is selected from the group consisting of carbon and sulfur, and wherein A and Z are different.

2. The method of claim 1 wherein said acaricide is present at a concentration of about 50 to 60,000 ppm in a composition comprising an inert carrier, and wherein said composition is applied to plants at a rate of from about 0.1 to about 3.0 lbs. of said acaricide per acre.

3. The method of claim 2 wherein said acaricide has the formula

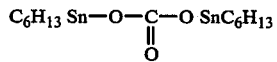

* * * * *

UNITED STATES PATENT AND TRADEMARK OFFICE
CERTIFICATE OF CORRECTION

PATENT NO. : 4,125,624
DATED : November 14, 1978
INVENTOR(S) : Francis J. Cracco and Wayne I. Fanta It is certified that error appears in the above-identified patent and that said Letters Patent are hereby corrected as shown below:

Col. 9, Table VII, under 7 days column, Control should be -- 10 --.

Col. 9, Table VIII, all of the ">" should be -- < --.

Signed and Sealed this

Tenth Day of April 1979

[SEAL]

Attest:

RUTH C. MASON
Attesting Officer

DONALD W. BANNER
Commissioner of Patents and Trademarks